United States Patent [19]
Burk et al.

[11] Patent Number: 6,017,953
[45] Date of Patent: *Jan. 25, 2000

[54] THROMBOXANE LIGANDS

[75] Inventors: Robert M. Burk, Laguna Beach; Achim H. Krauss, Foothill Ranch; David F. Woodward, Lake Forest, all of Calif.

[73] Assignee: Allergan Sales, Inc., Irvine, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/926,662

[22] Filed: Sep. 9, 1997

Related U.S. Application Data

[63] Continuation-in-part of application No. 08/832,431, Apr. 2, 1997, Pat. No. 5,741,812, which is a continuation-in-part of application No. 08/645,467, May 13, 1996, Pat. No. 5,650,431, which is a continuation-in-part of application No. 08/378,414, Jan. 26, 1995, Pat. No. 5,516,791, which is a division of application No. 08/174,534, Dec. 28, 1993, Pat. No. 5,416,106.

[51] Int. Cl.$^7$ .................... C07D 307/00; A61K 31/34
[52] U.S. Cl. .................................. 514/469; 549/463
[58] Field of Search ................................. 514/469; 549/463

[56] References Cited

U.S. PATENT DOCUMENTS

| | | | |
|---|---|---|---|
| 4,591,603 | 5/1986 | Das | 514/469 |
| 5,128,322 | 7/1992 | Glass | 514/19 |
| 5,128,354 | 7/1992 | Masuda et al. | 514/379 |
| 5,149,540 | 9/1992 | Kunihiro et al. | 424/489 |
| 5,248,507 | 9/1993 | Silva et al. | 424/643 |
| 5,264,220 | 11/1993 | Long, Jr. et al. | 424/450 |
| 5,382,569 | 1/1995 | Cody et al. | 514/17 |
| 5,389,630 | 2/1995 | Sato et al. | 514/218 |
| 5,409,956 | 4/1995 | Yoshida et al. | 514/562 |
| 5,415,863 | 5/1995 | Williams et al. | 424/427 |
| 5,436,260 | 7/1995 | Hodges et al. | 514/389 |
| 5,443,848 | 8/1995 | Kramer et al. | 424/643 |
| 5,447,712 | 9/1995 | White et al. | 514/110 |
| 5,476,846 | 12/1995 | Lardy et al. | 514/79 |
| 5,478,844 | 12/1995 | Aono et al. | 514/320 |
| 5,480,645 | 1/1996 | Della Valle et al. | 424/439 |
| 5,482,960 | 1/1996 | Berryman et al. | 514/64 |
| 5,504,090 | 4/1996 | Neely | 514/263 |
| 5,650,431 | 7/1997 | Burk | 514/450 |
| 5,741,812 | 4/1998 | Burk | 514/450 |

*Primary Examiner*—D. Margaret Seaman
*Attorney, Agent, or Firm*—Robert J. Baran; Carlos A. Fisher; Martin A. Voet

[57] ABSTRACT

A method of treating ocular hypotension, hypertension, hemorrhage, myocardial ischemia, angina pectoris, coronary contraction, cerebrovascular contraction after subarachnoidal hemorrhage, and asthma which comprises administering to a mammal suffering therefrom a therapeutically effective amount of a thromboxane ligand which is a compound formula I,

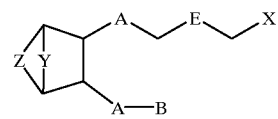

wherein Y is $(CH_2)_x$; Z is selected from the group consisting of O, $OCH_2$,

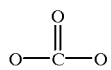

and $(CR_2)_x$, x is an integer of 1 or 2; $R_2$ is hydrogen or an alkyl radical of from 1 to 4 carbons, A is an alkylene or alkenylene radical having from two to seven carbon atoms, which radical may be substituted with one or more hydroxy, oxo, alkyloxy or alkylcarboxy groups or said alkylene or alkenylene may have one or more enchained oxo or imino radicals; B is a methyl radical or a cycloalkyl radical having from three to seven carbon atoms, or an aryl radical, selected from the group consisting of hydrocarbyl aryl and heteroaryl radicals wherein the heteroatom is selected from the group consisting of nitrogen, oxygen and sulfur atoms, or substituted derivatives of said methyl, cycloalkyl or aryl radicals wherein said substituent is selected from the group consisting of halo, nitro, amino, thiol, hydroxy, alkyloxy and alkylcarboxy; and X is selected from the group consisting of cyano, —COOR, —$CH_2OR$, —$C(O)N(R_2)$, —$CH_2N(R_2)$ —CH=N—OH and —$CH_2SR_1$ radicals wherein R is hydrogen or a $C_1$ to $C_{10}$ alkyl, phenyl or benzyl and E is O or S; or a pharmaceutically acceptable salt thereof.

18 Claims, 5 Drawing Sheets

6,017,953

THROMBOXANE LIGANDS

CROSS REFERENCE TO RELATED APPLICATIONS

This patent application is a continuation-in-part of U.S. patent application Ser. No. 832,431, filed on Apr. 2, 1997, now U.S. Pat. No. 5,741,812; which is a continuation in part of U.S. patent application Ser. No. 645,467, filed on May 13, 1996, now U.S. Pat. No. 5,650,431; which is a continuation in part of U.S. patent application Ser. No. 378,414, filed Jan. 26, 1995, now U.S. Pat. No. 5,516,791; which is a division of U.S. patent application Ser. No. 174,534, filed Dec. 28, 1993, now U.S. Pat. No. 5,416,106.

BACKGROUND OF THE INVENTION

1. Field of the Invention

The present invention relates to thromboxane receptor ligands including a carboxylic acid group derivative, which do not cause blood clotting. In particular, the thromboxane receptor ligands are bicyclic carboxylic acid and derivatives thereof wherein said bicyclic rings may be hydrocarbyl or oxohydrocarbyl, e.g. 7-[carboxyalkyl or alkenyl]-6-[alkyl or alkenyl]-3-oxo-2,4-dioxobicyclo[3.2.1] octanes and derivatives thereof. In particular, ester, hydroxyl, amino, amido, azido, oxime, thiol, ether and thiol ether derivatives of said carboxylic acid group are contemplated. In particular, 7-[6-carboxy-2-hexenyl]-6-[3-hydroxy-1-octenyl] 3-oxo-2,4-dioxobicyclo-[3.2.1] octane derivatives are disclosed. These compounds are useful as thromboxane agonists and antagonists. These compounds are also useful as ocular hypotensives.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Various U.S. Patents have recently issued which relate to thromboxane ligands and/or treating hemorrhaging. For example, U.S. Pat. Nos. 5,128,322; 5,128,354; 5,149,540; 5,389,630; 5,415,863; 5,436,260; 5,447,712; 5,482,960; 5,478,844 and 5,504,090 relate to methods of treating hemorrhaging. U.S. Pat. Nos. 5,248,507; 5,264,220; 5,382,569; 5,409,956; 5,443,848; 5,476,846; 5,480,645; 5,482,960 and 5,504,090 relate to thromboxane ligands. It is thus clear that a great deal of research is currently involved in thromboxane ligands, especially for treating hemorrhaging and related conditions.

SUMMARY OF THE INVENTION

We have found that certain bicyclic carboxylic acids and derivatives thereof, wherein said bicyclic rings may b e hydrocarbyl or oxy hydrocarbyl, e.g. 7-[carboxylalkyl or alkenyl]-6-[alkyl or alkenyl]-3-oxo-2,4-dioxobicyclo[3.2. 1] octane derivatives thereof, e.g. ester, hydroxyl, amino, amido, azido, oxime, thiol, ether and thiol ether derivatives of said carboxy group are potent ocular hypotensive agents. We have further found that these compounds are thromboxane ligands and may have the unique ability, described herein, to mimic the vasoconstrictor properties of thromboxane A2 and its endoperoxide precursors, without causing concomitant platelet aggregation, i.e. blood clotting, and therefore said compounds provide a diverse variety of medical uses. Their potent vasoconstrictor properties may be safely used in therapy as they do not cause the platelet aggregation and resultant thrombosis that would arise from using known thromboxane mimetics.

The vasoconstrictor properties would substantially reduce blood flow in blood vessels and could be used to prevent hemorrhaging associated with external or internal injuries without the risk of thrombosis. These compounds may also be used as surgical adjuncts to reduce the bleeding from incisions at any anatomical location. Similarly, these compounds would be useful in limiting the bleeding associated with tooth extraction. The ability of these compounds to prevent hemorrhage, without causing platelet aggregation and resultant thrombosis, allows their safe application in systemic diseases where hemorrhage occurs. For example, bleeding from the gastro-intestinal tract associated with hemorrhoids, inflammatory bowel diseases, or gastric and peptic ulcer may be prevented. Bleeding associated with stroke may be prevented. Bleeding associated with stroke may be reduced without causing thrombosis and a potentially fatal complication. Bleeding is also a frequent complication in retinal diseases and surgeries resulting in impaired vision. This would also be amenable to safe treatment by the vascular-selective thromboxane mimetics described herein. Excessive bleeding associated with menstruation, childbirth, and uterine dysfunction may also be safely treated.

The selective vasoconstrictor properties of these compounds may be used to treat systemic hypotension. They may also be employed to restore normal blood pressure in haemorragic, anaphylactic, or septic shock episodes, without the serious risks associated with typical thromboxane mimetics which would result from their pro-aggregatory effects on platelets.

The selective vasoconstrictor properties may also be used to provide local anti-inflammatory effects in tissues such as the eye, skin, and nose. They may also be used to limit plasma exudation in burns and scalds.

A thromboxane-like vasoconstrictor that does not cause platelet aggregation may also be useful in optimizing blood born delivery of drugs and diagnostics in encapsulating vehicles. For example, delivery of drugs or diagnostic substances encapsulated in heat-sensitive or light-sensitive liposomes to the retina may be safely enhanced by agents described herein which selectively produce vasoconstriction.

Additionally, certain of the bicyclic carboxylic acid derivatives of the present invention are useful as thromboxane antagonists for treating systemic or pulmonary hypertension, myocardial ischemia, angina pectoris, coronary contraction, cerebrovascular contraction after sub-arachnoidal hemorrhage, cerebral hemorrhage and asthma.

Finally, the profound ocular hypotensive activity of these cyclic carbonate compounds is unexpected, given that the benchmark thromboxane/endoperoxide mimetic U-46619 (Coleman, R. A., et.al., Br. J. Pharmacol. 73:773–778, 198 1) causes ocular hypertension in primates. The compounds herein would, therefore, be useful for treating glaucoma and ocular hypertension. They may be particularly useful as ocular surgical adjuncts for preventing ocular hypertensive episodes and reducing local bleeding that may occur post-surgically without complications inherent in blood clotting.

The present invention relates to methods of treating ocular hypertension and other diseases and conditions wherein thromboxane ligands are useful for treating which comprises administering an effective amount of a bicyclic carboxylic acid derivative represented by the formula I

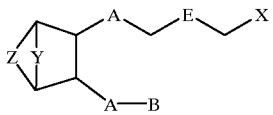

wherein Y is $(CH_2)_x$, Z is selected from the group consisting of O, $OCH_2$,

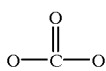

and $(CR_2)_x$, x is an integer of 1 or 2, $R_2$ is hydrogen or an alkyl radical of from 1 to 4 carbons, e.g. methyl, or ethyl;

A is an alkylene or alkenylene radical having from two to seven carbon atoms, e.g. about four to six carbon atoms, which radical may be substituted with one or more hydroxy, oxo, alkyloxy or alkylcarboxy groups or said alkylene or alkenylene may have one or more enchained oxo or imino radicals; B is a methyl radical or a cycloalkyl radical having from three to seven carbon atoms, e.g. about five to six carbon atoms, or an aryl radical, selected from the group consisting of hydrocarbyl aryl and heteroaryl radicals wherein the heteroatom is selected from the group consisting of nitrogen, oxygen and sulfur atoms; and X is selected from the group consisting of cyano, —COOR, —$CH_2OR$, —C(O)N($R_2$), —$CH_2N(R_2)$ —CH=N—OH and —$CH_2SR$ radicals, wherein R is hydrogen or $C_1$ to $C_{10}$ alkyl, phenyl or benzyl and E is O or S; or a pharmaceutically acceptable salt thereof. For example, A may be a straight chain alkylene radical, e.g. heptylene, or alkenylene radical, e.g. 3-hydroxy-1-heptylenyl, or an ethylenyloxyethylenyl radical or amino carbonyl hydrazino methyl radical and B may be selected from the group consisting of methyl, cyclopentyl, cyclohexyl, phenyl, thienyl, furanyl, pyridyl, etc. B may also be substituted by radicals selected from the group consisting of halo, e.g. fluoro, chloro, iodo etc., nitro, amino, thiol, hydroxy, alkyloxy, alkylcarboxy, etc. Preferably, B is methyl, cyclohexyl or phenyl.

BRIEF DESCRIPTION OF THE DRAWINGS

The Drawing Figures outline the reaction scheme of the Example, below, wherein representative compounds of the invention, having either an alkyl or alkenyl alpha chain are prepared and the numbered compounds are as described therein.

DETAILED DESCRIPTION OF THE INVENTION

Figure 1:
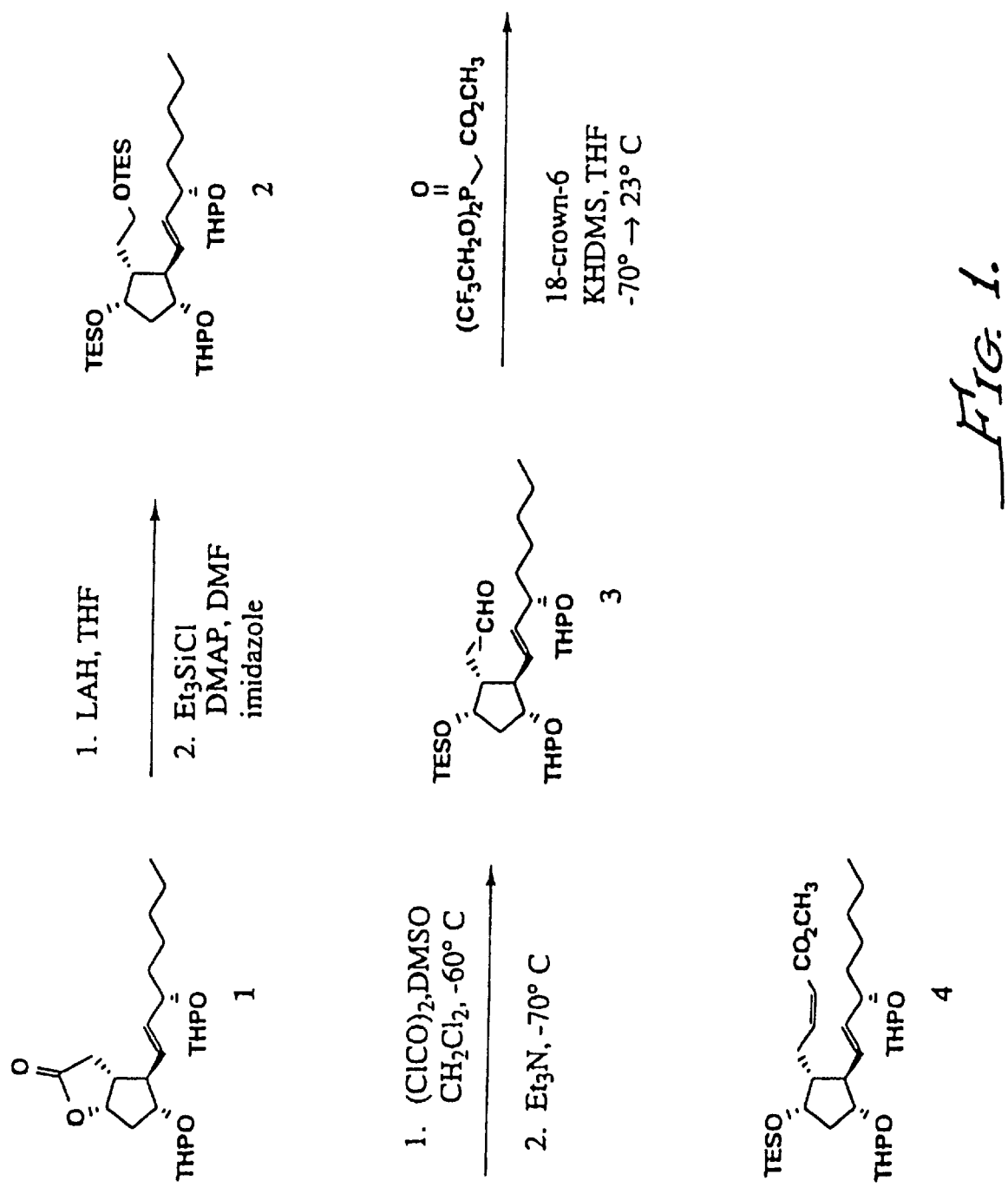
FIG. 1 outlines the reaction scheme of the Example wherein BIS-TES ether 2, Aldehyde 3 and α, β-Unsaturated ester 4 are obtained.
Figure 2:
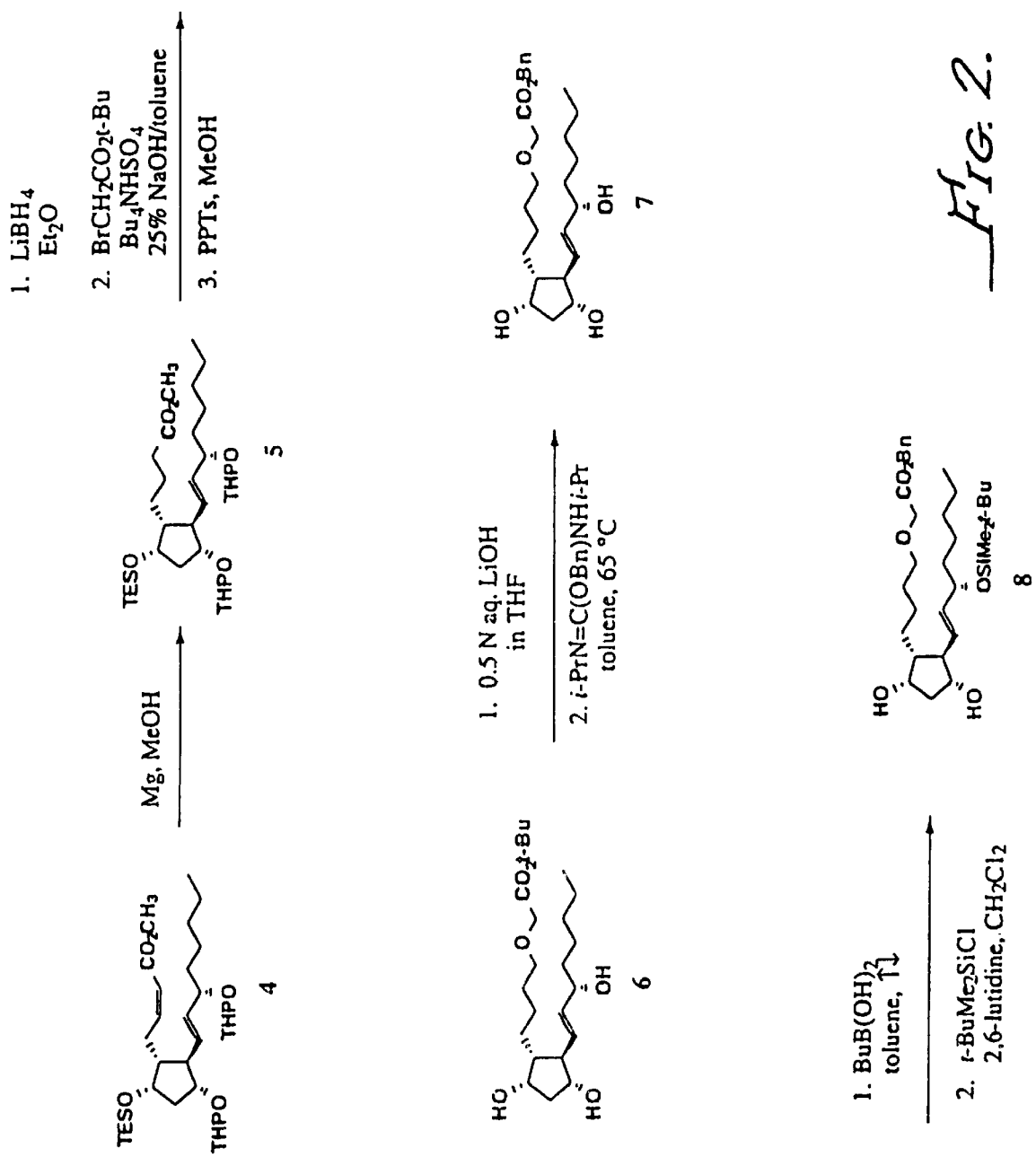
FIG. 2 outlines the reaction scheme of the Example wherein Ester 5, Triol 6, Benzylester 7 and TBDMS Ether 8 are obtained.
Figure 3:
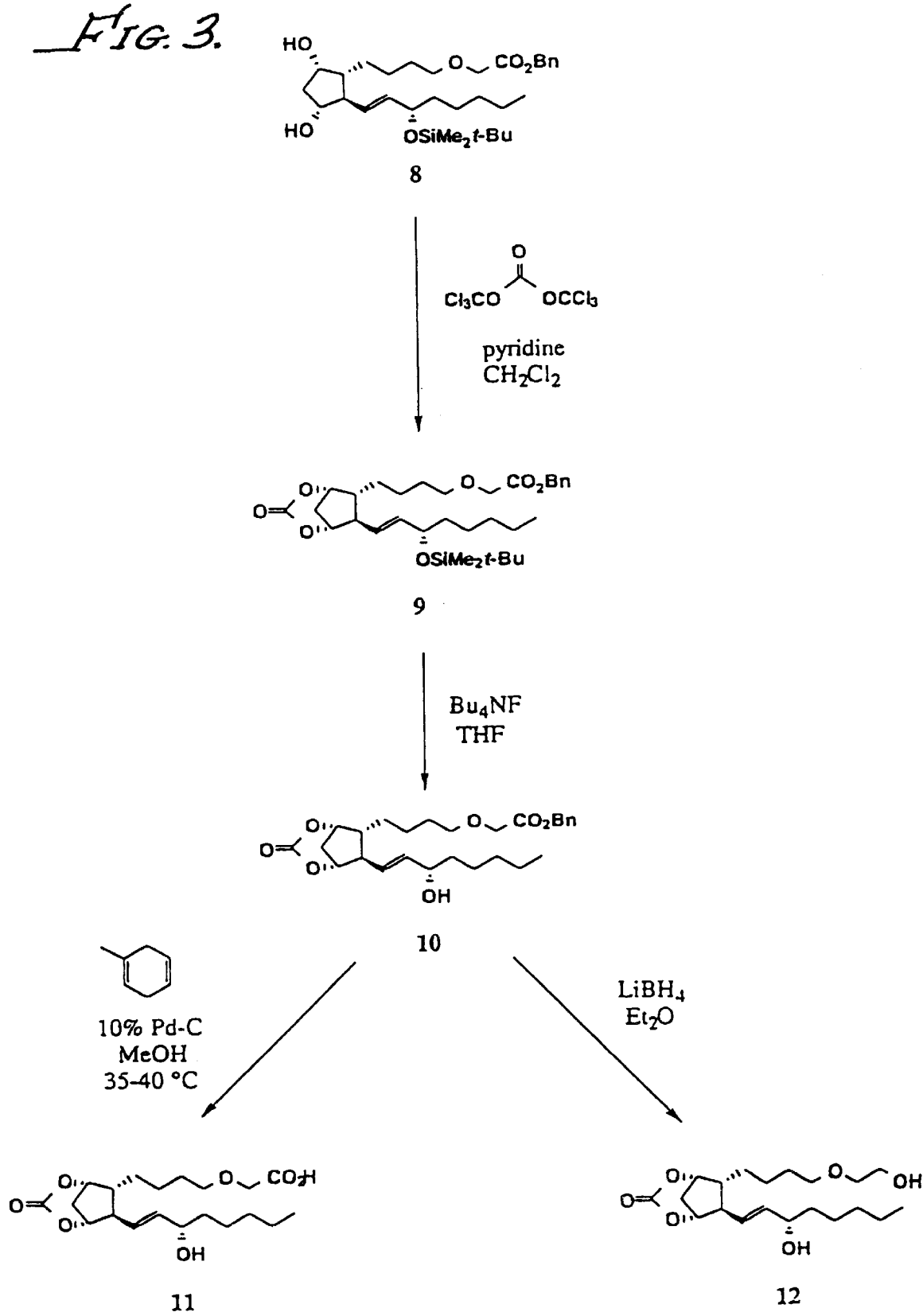
FIG. 3 outlines the reaction scheme of the Example wherein Cyclic carbonate 9, 15-Hydroxybenzyl ester 10, Hydroxy Acid 11 and Diol 12 are obtained.
Figure 4:
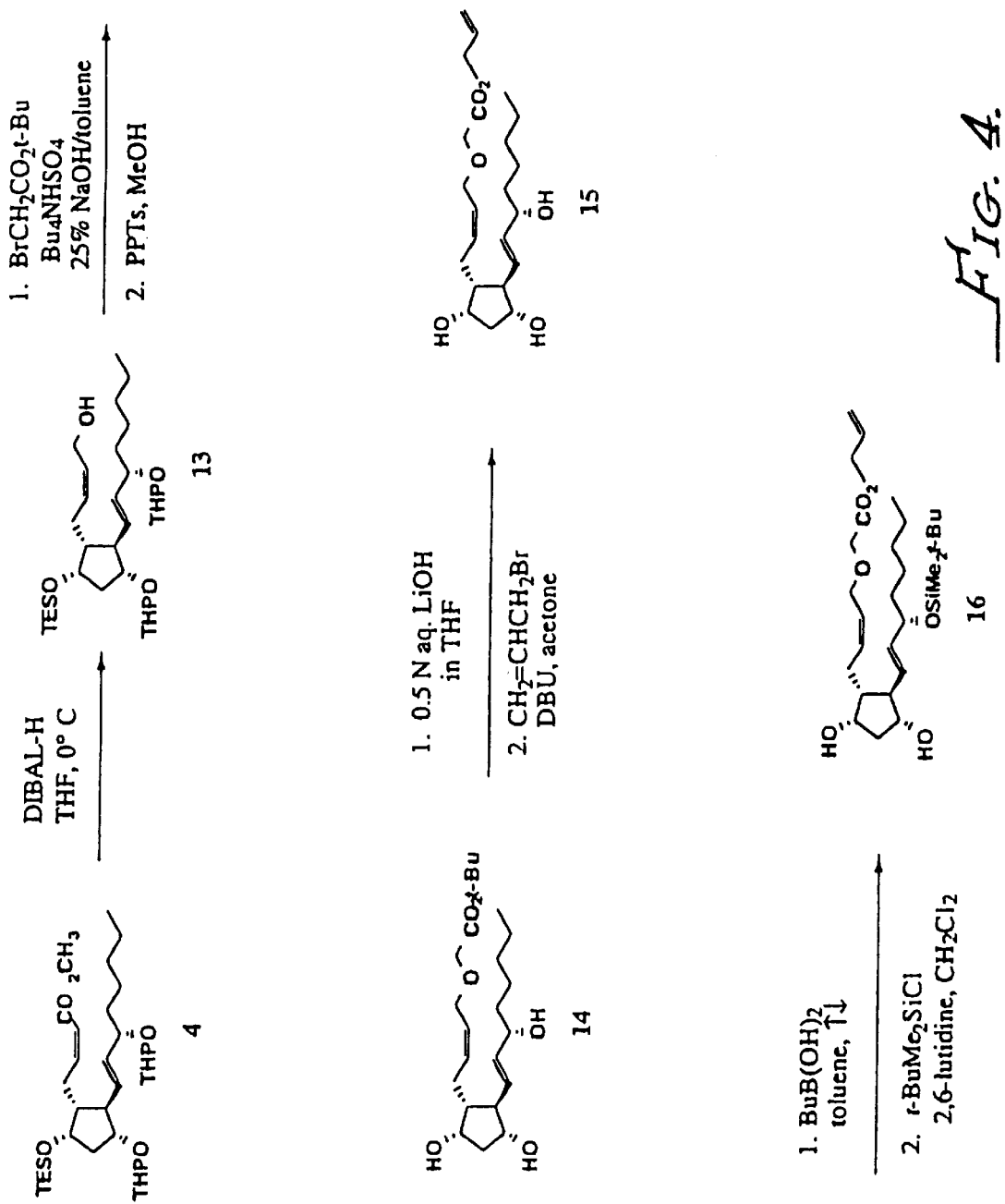
FIG. 4 outlines the reaction scheme of the Example wherein 2-Allylic Alcohol 13, t-Butyl Ester 14, Allyl Ester 15 and 15-TBDMS Ether 16 are obtained.
Figure 5:
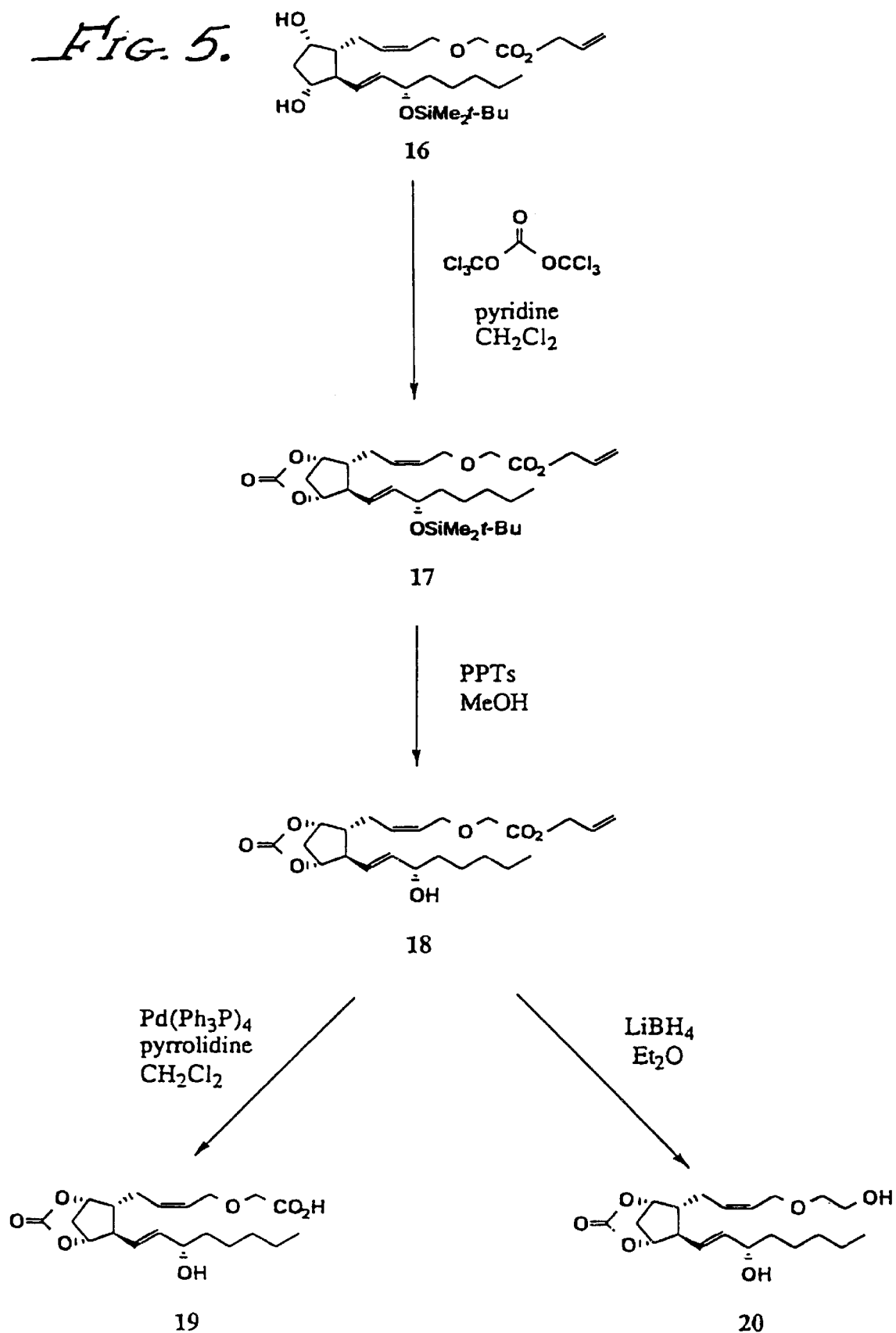
FIG. 5 outlines the reaction scheme of the Example wherein Cyclic Carbonate 17, 15-Hydroxy Allyl Ester 18, 15-Hydroxy Acid 19 and Diol 20 are obtained.

The present invention relates to the use of the compounds of Formula I, above, as ocular hypotensives or a thromboxane ligands.

Preferably, the present invention relates to the use of a 7-[carboxylalkyl or alkenyl]-6-[alkyl or alkenyl]-3-oxo-2,4-dioxobicyclo[3.2.1] octane or derivative thereof, e.g. an ester, hydroxyl, amino, amido, azido, oxime, thiol, ether or thiol ether derivative as thromboxane ligands. These preferred therapeutic agents are represented by compounds having the formula II,

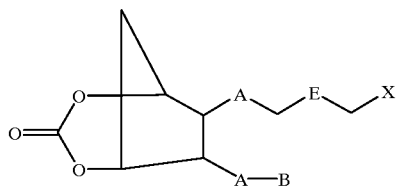

wherein A, B and X are as defined above.

For the purpose of this invention, unless further limited, the term "aliphatic" means linear and branched alkylene and alkenylene radicals, the terms "alkylene" and "alkenylene" mean divalent radicals derived from alkanes and alkenes, respectively. The term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about six, preferably one to about four carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

More preferably the method of the present invention comprises administering a 7-[carboxyalkyl or alkenyl]-6-[alkyl or alkenyl]-3-oxo-2,4-dioxobicyclo[3.2.1] octane derivative represented by the formula III,

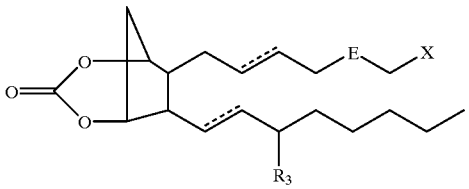

wherein either the α or ω chain may be unsaturated, i.e. the dashed bonds represent a single bond or a double bond which can be in the cis or trans configuration and $R_3$ is =O, —$OR_1$ or —$O(CO)R_6$; wherein $R_1$ is hydrogen or an alkyl radical having from 1 to about 5 carbon atoms and $R_6$ is a saturated or unsaturated acyclic hydrocarbon group having from 1 to about 20 carbon atoms, or —$(CH_2)_m R_7$ wherein m is 0–10, preferably 0–4; and $R_7$ is an aliphatic ring from about 3 to about 7 carbon atoms, or an aryl or heteroaryl ring, as defined above; or a pharmaceutically acceptable salt thereof.

Preferably the derivative used in the above method of treatment is a compound of formula IV,

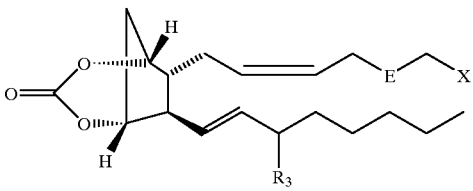

wherein hatched lines indicate the α configuration and a solid triangle is used to indicate the β configuration.

As an aromatic ring, $R_7$ preferably is phenyl, and the heteroaromatic rings have oxygen, nitrogen or sulfur as a heteroatom, i.e., $R_7$ may be thienyl, furanyl, pyridyl, etc.

In a further aspect, the present invention relates to pharmaceutical compositions comprising a therapeutically effective amount of a compound of formulae (I), (II), (III) or IV wherein the symbols have the above meanings, or a pharmaceutically acceptable salt thereof in admixture with a non-toxic, pharmaceutically acceptable carrier or liquid vehicle.

Preferred representatives of the compounds within the scope of the present invention are the compounds of formula IV wherein X are —COOR, —$CH_2OH$ and —$C(O)N(R)_2$, wherein R is defined above, and the pharmaceutically acceptable salts thereof. Specific compounds within the scope of this invention are as follows:

Benzyl 7-[7-(3α-Hydroxy-1E-octenyl)-3-oxo-2α, 4α-dioxobicyclo [3.2.1]octan-6-yl]-2-oxa-heptanoate Allyl 7-[7-(3α-Hydroxy-1E-octenyl)-3-oxo-2α, 4α-dioxobicyclo [3.2.1]octan-6-yl]-2-oxa-5Z-heptanoate 7-[7-(3α-Hydroxy-1E-octenyl)-3-oxo-2α, 4α-dioxobicyclo [3.2.1]octan-6-yl]-2-oxa-heptanoic acid 7-[7-(3α-Hydroxy-1E-octenyl)-3-oxo-2α, 4α-dioxobicyclo [3.2.1]octan-6-yl]-2-oxa-5Z-heptenoic acid 7-[7-(3α-Hydroxy-1E-octenyl)-3-oxo-2α, 4α-dioxobicyclo [3.2.1]octan-6-yl]-2-oxa-5Z-hepten-1-ol 7-[7-(3α-Hydroxy-1E-octenyl)-3-oxo-2α, 4α-dioxobicyclo [3.2.1]octan-6-yl]-2-oxa-heptan-1-ol A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, amines, etc.

The compounds utilized in the method of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I through IV or a corresponding pharmaceutically acceptable salt of a compound of Formula 1 through IV.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active compounds is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit: doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use, the compounds utilized in the method of this invention are administered at the initial dosage of about 0.01 mg to about 10 mg/kg daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Pharmaceutical compositions for treating glaucoma or lowering intraocular pressure may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with a n appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, (sodium EDTA) although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 $\mu$l.

This invention is further illustrated by the following non-limiting examples.

EXAMPLE

Bis-TES ether 2.

A solution of the previously reported lactone 1 (7.41 g, 0.017 mol) in THF (40 mL) was cooled to 0° C. and lithium aluminum hydride (21.0 mL of a 1.0M solution in THF, 0.021 mol) was added dropwise. (See Corey, E. J.; Weinshanker, N. M.; Schaaf, T. K. and Huber, W. *J. Am. Chem. Soc.*, 1969, 91, 5675.) After 2h the reaction solution was poured into a stirred mixture of ice-cold EtOAc/saturated aqueous NH$_4$Cl. The resultant mixture was stirred for 1 h and then extracted with EtOAc (2×). The combined organic portions were washed with brine, dried (MgSO$_4$), filtered and concentrated in vacuo to afford a clear, viscous oil.

The residue was diluted with DMF (90 mL) then 4-dimethylaminopyridine (595 mg, 0.005 mol) and imidazole (3.6 g, 0.052 mol) were added followed by chlorotriethylsilane (6.5 mL, 0.039 mol). The reaction was stirred for 12h, diluted with Et$_2$O and washed with 1N HCl, water, saturated aqueous NaHCO$_3$ and brine. The organic portion was dried (MgSO$_4$), filtered and concentrated in vacuo. Flash column chromatography (silica gel, 19:1 hex/EtOAc) provided 11.24 g (99%) of the titled compound 2 as a clear, colorless oil.

Aldehyde 3.

Methyl sulfoxide (0.41 mL, 5.65 mmol) was added to a solution of oxalyl chloride (1.4 mL of a 2.0 M solution in CH$_2$Cl$_2$, 2.83 mmol) in CH$_2$Cl$_2$ (3.0 mL) at −70° C. After 10 minutes a solution of 2 (1.26 g, 1.88 mmol) in CH$_2$Cl$_2$(4.5 mL) as added and the reaction was stirred at −50° C. for 2.5 h. The reaction solution was recooled to −70° C., triethylamine (1.2 mL, 8.88 mmol) was added, and the reaction was allowed to warm to room temperature. Water was added and the mixture was extracted with EtOAc. The organic portion was washed with water, brine, dried (MgSO$_4$), filtered and concentrated in vacuo.

FCC (silica gel, 9:1 hex/EtOAc) afforded 0.94 g (91%) of aldehyde 3.

α,β-Unsaturated ester 4.

Potassium bis(trimethylsilyl)amide (11.1 mL of a 0.5M solution in toluene, 5.55 mmol) was added to a solution of bis (2,2,2-trifluoroethyl)(methoxycarbonylmethyl) phosphonate (1.77 g, 5.55 mmol) and 18-crown-6(4.02 g, 15.2 mmol) in THF (20 mL) at −70° C. After 0.5 h a solution of the aldehyde 3 (2.80 g, 5.07 mmol) in THF (10 mL) was added. The reaction was stirred at −70° C. for 2 h, warmed to 0° C. for 2 h and then quenched with saturated aqueous NH$_4$Cl. After warming to room temperature the mixture was extracted with EtOAc and the organic portion was washed with water (2×), brine, dried (MgSO$_4$), filtered and concentrated in vacuo. FCC (silica gel, 8:1 hex/EtOAc) gave 2.22 g (70%) of pure cis-4 and 0.78 g (25%) of a mixture of cis-trans 4.

Ester 5.

Magnesium turnings (520 mg, 21.4 mmol) were added to a solution of 4 (1.33 g, 2.14 mmol) in anhydrous MeOH (18 mL) at 23° C. After 12 h the reaction was quenched with 3N HCl, stirred 10 minutes and extracted with Et$_2$O(2×). The combined organics were washed with saturated aqueous NaHCO$_3$ brine, dried (MgSO$_4$), filtered and concentrated in vacuo. FCC(9:1 hex/EtOAc) gave 0.78 g (58%) of the saturated ester 5.

Triol 6.

A mixture of the ester 5 (0.78 g, 1.25 mmol) and lithium borohydride (55 mg, 2.50 mmol) in anhydrous Et$_2$O(5 mL) was stirred at 23° C. for 2 h. The reaction was quenched with 1N NaOH, stirred for 0.5 h and extracted with EtOAc. The organic portion was washed with brine, dried (MgSO$_4$), filtered and concentrated in vacuo to afford the intermediate alcohol as a clear, colorless oil.

A mixture of the crude alcohol, tetrabutyl ammonium hydrogen sulfate (307 mg, 0.91 mmol) t-butyl bromoacetate (1.95 g, 9.98 mmol) and 25% w/w aqueous NaOH (11.4 mL) in toluene (17.0 mL) was vigorously stirred at 23° C. for 16 h. The reaction mixture was extracted with EtOAc (2×) and the combined organics were washed with brine, dried (MgSO$_4$), filtered and concentrated in vacuo to give the intermediate ester as a clear, colorless oil.

Pyridinium p-toluenesulfonate (330 mg, 1.31 mmol) was added to a solution of the crude t-butyl ester in MeOH (7.5 mL) at 23° C. After stirring for 16 h the solvent was removed in vacuo. The residue was diluted with EtOAc and then washed with 1N HCl, saturated aqueous NaHCO$_3$, brine dried (MgSO$_4$), filtered and concentrated in vacuo, FCC (100% EtOAc), silica gel) provided 233.8 mg (60%) of triol 6.

Benzyl ester 7.

A mixture of t-butyl ester 6 (320 mg, 0.77 mmol) and lithium hydroxide (3.0 mL of a 0.5N solution in H$_2$O, 1.5 mmol) in THF (6.0 mL) was heated to 55° C. for 2 h. The reaction was cooled to room temperature, acidified with 1N HCl and extracted with EtOAc (2×). The combined organics were washed with brine (2×), dried (MgSO$_4$), filtered and concentrated in vacuo.

A solution of the residue and O-benzyl-N,N'-diisopropylisourea (910 mg, 3.85 mmol) in benzene (8.0 mL) was heated to 60° C. for 12 h. The solvent was removed in vacuo and the residue was purified by FCC(silica gel, 100% EtOAc) to afford 343 mg (99%) of the benzyl ester 7 as a clear, viscous oil.

TBDMS Ether 8.

A solution of 7 (343 mg, 0.76 mmol) and phenyl boronic acid (103.3 mg, 0.85 mmol) in CH$_2$Cl$_2$ (4.5 mL) was heated to reflux for 12 h with azeotropic removal of water. The solution was cooled to 0° C. and 2,6-lutidine (0.36 mL, 3.08 mmol) was added followed by t-butyldimethylsilyl trifluoromethane-sulfonate (0.53 mL, 2.31 mmol) in CH$_2$Cl$_2$ (4.5 mL). After 12 h the solvent was removed in vacuo and the residue was diluted with EtOAc. The organic portion was washed with 1N NaOH (2×), 1N HCl, brine, then dried (MgSO$_4$), filtered and concentrated in vacuo. FCC (silica gel, 2:1 hex/EtoAc) gave 137 mg (32%) of the silyl ether 8.

Cyclic Carbonate 9.

A solution of the diol (137 mg, 0.243 mmol) and pyridine (0.10 mL, 1.21 mmol) in CH$_2$Cl$_2$ (2.0 mL) was cooled to −70° C. Triphosgene (43.2 mg, 0.145 mmol) in CH$_2$Cl$_2$ (1.0 mL) was added and the reaction was allowed to warm to room temperature on its own accord. The reaction was quenched with saturated aqueous NH$_4$Cl and extracted with EtOAc. The organic portion was washed with 1N HCl, saturated aqueous NaHCO$_3$, brine, dried (MgSO$_4$), filtered and concentrated in vacuo. FCC (silica gel, 3:1 hex/EtOAc) afforded 68.3 mg (48%) of 9 as a colorless oil.

15-Hydroxybenzyl ester 10.

Tetrabutylammonium fluoride (0.23 mL of a 1.0M solution in THF, 0.23 mmol) was added to a solution of the silyl ether 9 (68 mg, 0.115 mmol) in THF (1.0 mL) at 23° C. After 2 h the reaction was diluted with EtOAc and washed with H$_2$O, brine, dried (MgSO$_4$), filtered and concentrated in vacuo. FC (silica gel, 1:1 hex/EtOAc) provided 24.2 mg (44%) of alcohol 10 as a viscous oil.

Hydroxy Acid 11.

A suspension of 10% by weight palladium on carbon (8 mg) and benzyl ester 10 (24 mg, 0.05 mmol) in 4:1 MeOH/1-methyl-1,4-cyclohexadiene (1.25 mL) was heated at 35–40° C. for 0.25 h. The reaction was diluted with EtOAc and filtered through celite. The filtrate was concentrated in vacuo to give 34.1 mg (70%) of carboxylic acid 11.

Diol 12.

Lithium borohydride (60 mL of a 2.0M solution in THF, 0.12 mmol) was added to a solution of the benzyl ester 10 (60 mg, 0.13 mmol) in anhydrous Et$_2$O (2.0 mL) cooled to 0° C. After 0.5 h the reaction was quenched with 1N NaOH, warmed to room temperature and extracted with EtOAc. The organic portion was washed with brine, dried ($MgSO_4$), filtered and concentrated in vacuo. Purification by FCC (silica gel, 100% EtOAc) have 32.8 mg (70%) of diol 12 as a clear, colorless oil.

2-Allylic Alcohol 13.

Diisobutylaluminum hydride (11.9 mL of a 1.0 M solution in toluene, 11.9 mmol) was added to a solution of ene-ester 4 (2.46 g, 3.95 mmol) in THF (16 mL) at 0° C. After 2 h the reaction was quenched with MeOH (0.53 mL, 13.0 mmol). The gelatinous mixture was warmed to room temperature, treated with 1N NaOH and stirred for 1 h. The resultant mixture was extracted with EtOAc and the organic portion was washed with brine, dried ($MgSO_4$), filtered and concentrated in vacuo. FCC (silica gel, 2:1 hex/EtOAc) gave 2.22 g (97%) of allylic alcohol 13.

t-Butyl Ester 14.

A mixture of the alcohol (1.5 g, 2.58 mmol), tetrabutylammonium hydrogen sulfate (635, 9 mg, 1.87 mmol), 25% w/w aqueous NaOH (23.8 mL) and t-butyl bromoacetate (3.0 mL, 20.64) in toluene (35 mL) was stirred vigorously at 23° C. for 16 h. The reaction mixture was extracted with EtOAc (2×). The combined organics were washed with brine, dried ($MgSO_4$), filtered and concentrated in vacuo to give a clear, odorless oil.

A solution of the product obtained above and pyridinium p-toluene sulfonate (648.3 mg, 2.58 mmol) in MeOH (10.3 mL) was stirred at 23° C. for 16 h. The solvent was removed in vacuo and the residue was diluted with EtOAc then washed with 1N HCl, saturated aqueous $NaHCO_3$, and brine. The organic portion was dried ($MgSO_4$), filtered and concentrated in vacuo. Purification by FCC (silica gel, 100% EtOAc) followed by 19:1 EtOAc/MeOH) afforded 810 mg (76%) of trihydroxy t-butyl ester 14.

Allyl Ester 15.

A mixture of t-butyl ester 14 (1.01 g, 2.45 mmol) and lithium hydroxide (14.6 mL of a 0.5 N aqueous solution, 7.3 mmol) in THF (29 mL) was stirred for 12 h at 23° C. The resultant solution was acidified with 1N HCl and extracted with EtOAc (2×). The combined organics were washed with brine (2×), dried ($MgSO_4$), filtered and concentrated in vacuo.

The crude acid was diluted with acetone (10 mL) and 1,8-diazabicyclo [5.4.0] undec-7-ene (0.73 mL, 4.9 mmol) was added followed by allyl bromide (0.85 mL, 9.8 mmol). After stirring for 16 h at 23° C. the solvent was removed in vacuo. The residue was diluted with EtOAc and washed with 1N NCl, saturated aqueous $NaHCO_3$ and brine. The organic portion was dried ($MgSO_4$), filtered and concentrated in vacuo. FCC (silica gel, 3:1 EtOAc/hexane) afforded 720 mg (74%) of the allyl ester 15 as a clear, colorless oil.

15-TBDMS Ether 16.

A solution of triol 15 (720 mg, 1.82 mmol) and phenyl boronic acid (243.9 mg, 2.0 mmol) in $CH_2Cl_2$ (20 mL) was heated to reflux with azeotropic removal of water. After 4 h the reaction was cooled to 0° C. and treated with 2,6-lutidine (0.85 mL, 7.27 mmol) followed by t-butyldimethylsilyl trifluoromethanesulfonate (1.3 mL, 5.45 mmol) and allowed to warm to room temperature. After 24 h the reaction w a s quenched with 1N NaOH and stirred for 0.5 h. The mixture was diluted with EtOAc and washed with 10% aqueous NaOH (2×). The organic portion was washed with 1N HCl, saturated aqueous $NaHCO_3$, brine then dried ($MgSO_4$), filtered and concentrated in vacuo. Purification of the residue by FCC (silica gel, 2:1 hex/EtOAC) provided 444 mg (48%) of silyl ether Cyclic Carbonate 17.

A solution of triphosgene (155 mg, 0.52 mmol) in $CH_2Cl_2$ (1.0 mL) was added the diol 16 (444 mg, 0.87 mmol) and pyridine (0.35 mL, 4.35 mmol) in $CH_2Cl_2$ (6.0 mL) at −70° C. The reaction was allowed to warm to room temperature on its own accord and after 24 h it was quenched with saturated aqueous $NH_4Cl$. The resultant mixture was extracted with EtOAc. The organic portion was washed with 1N HCl, saturated aqueous $NaHCO_3$, brine, dried ($MgSO_4$), filtered and concentrated in vacuo. Purification by FCC (silica gel, 3:1 hex/EtOAc) gave 133.8 mg (29%) of the cyclic carbonate 17 as a light yellow oil.

15-Hydroxy Allyl Ester 18.

A solution of silyl ether 17 (133 mg, 0.25 mmol) and pyridinium p-toluenesulfonate (62.4 mg, 0.25 mmol) in MeOH (1.5 mL) was stirred at 23° C. for 16 h. The solvent was removed in vacuo and the residue was diluted with EtOAc then washed with 1N HCl, saturated aqueous $NaHCO_3$ and brine. The organic portion was dried ($MgSO_4$), filtered and concentrated in vacuo. Purification by FCC (silica gel, 1:1 hex/EtOAc) gave 70.8 mg (68%) of title compound 18 as a clear, colorless oil.

15-Hydroxy Acid 19.

Pyrrolidine (69 mL, 0.83 mmol) was added to a solution of allyl ester 18 (35 mg, 0.083 mmol) and tetrakis-(triphenylphosphine)palladium(O) (9.6 mg, 0.008 mmol) i n $CH_2Cl_2$ (1.5 mL) cooled to 0° C. After 115 minutes the reaction was diluted with EtOAc and washed with IN HCl followed by brine (2×). The organic portion was dried ($Na_2SO_4$), filtered and concentrated in vacuo. Purification through a Sep-Pak cartridge (silica gel, 3:1 EtOAc/MeOH) afforded 27.0 mg (85%) of free acid 19.

Diol 20.

Lithium borohydride (41 mL, 0.083 mmol) was added to a solution of allyl ester (35 mg, 0.083 mmol) in anhydrous $Et_2O$ (1.5 mL) cooled to 0° C. After 0.5 h the reaction was quenched with 1N NaOH, warmed to room temperature and extracted with EtOAc. The organic portion was washed with brine, dried ($MgSO_4$), filtered and concentrated in vacuo. The residue was purified by FCC (silica gel, 100% EtOAc) to yield 21.5 mg (70%) of diol 20 as a clear, colorless oil.

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

I claim:

1. A compound of formula II useful as a thromboxane ligand,

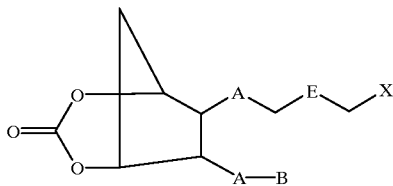

wherein Y is $(CH_2)_x$; Z is selected from the group consisting of O, $OCH_2$,

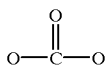

and $(CR_2)_x$, x is an integer of 1 or 2; $R_2$ is hydrogen or an alkyl radical of from 1 to 4 carbons, A is an alkylene or alkenylene radical having from two to seven carbon atoms, which radical may be substituted with one or more hydroxy, oxo, alkyloxy or alkylcarboxy groups or said alkylene or alkenylene may have one or more enchained oxo or imino radicals; B is a methyl radical or a cycloalkyl radical having from three to seven carbon atoms, or an aryl radical, selected from the group consisting of hydrocarbyl aryl and heteroaryl radicals wherein the heteroatom is selected from the group consisting of nitrogen, oxygen and sulfur atoms, or substituted derivatives of said methyl, cycloalkyl or aryl radicals wherein said substituent is selected from the group consisting of halo, nitro, amino, thiol, hydroxy, alkyloxy and alkylcarboxy; and X is selected from the group consisting of cyano, —COOR, —$CH_2OR$, —$C(O)N(R_2)$, —$CH_2N(R_2)$ —CH=N—OH and —$CH_2SR_1$ radicals wherein R is hydrogen or a $C_1$ to $C_{10}$ alkyl, phenyl or benzyl and E is O or S; or a pharmaceutically acceptable salt thereof.

2. A method of treating systemic hypertension, pulmonary hypertension, myocardial ischemia, angina pectoris, coronary contraction, cerebrovascular contraction after subarachnoidal hemorrhage, hemorrhage and asthma which comprises administering to a mammal suffering therefrom a therapeutically effective amount of a thromboxane ligand which is a compound formula II,

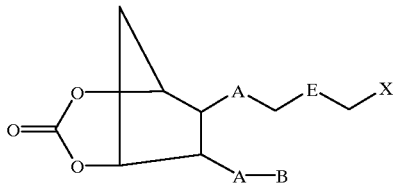

wherein Y is $(CH_2)_x$; Z is selected from the group consisting of O, $OCH_2$,

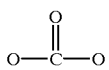

and $(CR_2)_x$, x is an integer of 1 or 2; $R_2$ is hydrogen or an alkyl radical of from 1 to 4 carbons, A is an alkylene or alkenylene radical having from two to seven carbon atoms, which radical may be substituted with one or more hydroxy, oxo, alkyloxy or alkylcarboxy groups or said alkylene or alkenylene may have one or more enchained oxo or imino radicals; B is a methyl radical or a cycloalkyl radical having from three to seven carbon atoms, or an aryl radical, selected from the group consisting of hydrocarbyl aryl and heteroaryl radicals wherein the heteroatom is selected from the group consisting of nitrogen, oxygen and sulfur atoms, or substituted derivatives of said methyl, cycloalkyl or aryl radicals wherein said substituent is selected from the group consisting of halo, nitro, amino, thiol, hydroxy, alkyloxy and alkylcarboxy; and X is selected from the group consisting of nitro, cyano, —COOR, —$CH_2OR$, —$C(O)N(R_2)$, —$CH_2N(R_2)$ —CH=N—OH and —$CH_2SR_1$ radicals wherein R is hydrogen or a $C_1$ to $C_{10}$ alkyl, phenyl or benzyl and E is O or S; or a pharmaceutically acceptable salt thereof.

3. A method of treating ocular hypertension and glaucoma which comprises administering to a mammal suffering therefrom a therapeutically effective amount of a thromboxane ligand which is a compound formula II,

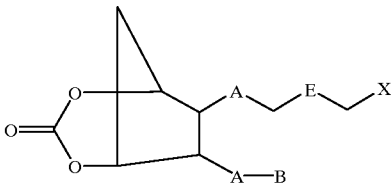

wherein Y is $(CH_2)_x$; Z is selected from the group consisting of O, $OCH_2$,

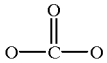

and $(CR_2)_x$, x is an integer of 1 or 2; $R_2$ is hydrogen or an alkyl radical of from 1 to 4 carbons, A is an alkylene or alkenylene radical having from two to seven carbon atoms, which radical may be substituted with one or more hydroxy, oxo, alkyloxy or alkylcarboxy groups or said alkylene or alkenylene may have one or more enchained oxo or imino radicals; B is a methyl radical or a cycloalkyl radical having from three to seven carbon atoms, or an aryl radical, selected from the group consisting of hydrocarbyl aryl and heteroaryl radicals wherein the heteroatom is selected from the group consisting of nitrogen, oxygen and sulfur atoms, or substituted derivatives of said methyl, cycloalkyl or aryl radicals wherein said substituent is selected from the group consisting of halo, nitro, amino, thiol, hydroxy, alkyloxy and alkylcarboxy; and X is selected from the group consisting of nitro, cyano, —COOR, —$CH_2OR$, —$C(O)N(R_2)$, —$CH_2N(R_2)$ —CH=N—OH and —$CH_2SR_1$ radicals wherein R is hydrogen or a $C_1$ to $C_{10}$ alkyl, phenyl or benzyl and E is O or S; or a pharmaceutically acceptable salt thereof.

4. The compound of claim 1 wherein said compound is a compound of formula III,

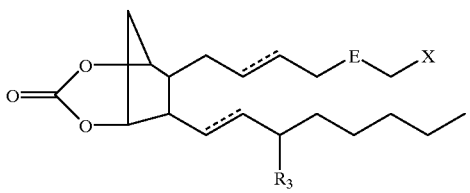

wherein either the α or ω chain may be unsaturated, i.e. the dashed bonds represent a single bond or a double bond which can be in the cis or trans configuration and $R_3$ is =O, —OR, or —O(CO) $R_6$; wherein $R_1$ is hydrogen or an alkyl radical having from 1 to about 5 carbon atoms and $R_6$ is a saturated or unsaturated acyclic hydrocarbon group having from 1 to about 20 carbon atoms, or —$(CH_2)_m R_7$ wherein m is 0–10, and $R_7$ is an aliphatic ring having from about 3 to about 7 carbon atoms, or an aryl radical selected from the group consisting of hydrocarbyl aryl and heteroaryl radicals wherein the heteroatom is selected from the group consisting of nitrogen, oxygen and sulfur atoms; or a pharmaceutically acceptable salt thereof.

5. The compound of claim 4 wherein said compound is a compound of formula IV,

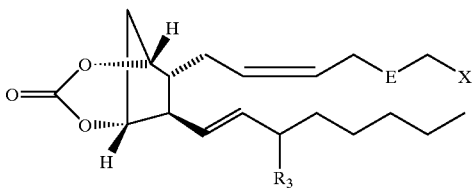

wherein the hatched line indicates the α configuration and the solid triangle indicates the β configuration.

6. The compound of claim 5 wherein X is selected from the group consisting of —COOR, —$CH_2OR$, —$CH2N(R_2)$ and -C(O)N(R2).

7. The compound of claim 6 wherein the compound is selected from the group consisting of
Benzyl 7-[7-(3α-Hydroxy-1E-octenyl)-3-oxo-2α, 4α-dioxobicyclo [3.2.1]octan-6-yl]-2-oxa-heptanoate
Allyl 7-[7-(3α-Hydroxy-1E-octenyl)-3-oxo-2α, 4α-dioxobicyclo [3.2.1]octan-6-yl]-2-oxa-5Z-heptanoate
7-[7-(3α-Hydroxy-1E-octenyl)-3-oxo-2α, 4α-dioxobicyclo [3.2.1]octan-6-yl]-2-oxa-heptanoic acid
7-[7-(3α-Hydroxy-1E-octenyl)-3-oxo-2α, 4α-dioxobicyclo [3.2.1]octan-6-yl]-2-oxa-5Z-heptenoic acid
7-[7-(3α-Hydroxy-1E-octenyl)-3-oxo-2α, 4α-dioxobicyclo [3.2.1]octan-6-yl]-2-oxa-5Z-hepten-1-ol
7-[7-(3α-Hydroxy-1E-octenyl)-3-oxo-2α, 4 60-dioxobicyclo [3.2.1]octan-6-yl]-2-oxa-heptan-1-ol.

8. The compound of claim 7 wherein said compound is Benzyl 7-[7-(3α-Hydroxy-1E-octenyl)-3-oxo-2α, 4α-dioxobicyclo [3.2.1]octan-6-yl]-2-oxa-heptanoate.

9. The compound of claim 7 wherein said compound is Allyl 7-[7-(3α-Hydroxy-1E-octenyl)-3-oxo-2α, 4α-dioxobicyclo [3.2.1]octan-6-yl]-2-oxa-5Z-heptanoate.

10. The compound of claim 7 wherein said compound is 7-[7-(3α-Hydroxy-1E-octenyl)-3-oxo-2α, 4 60-dioxobicyclo [3.2.1]octan-6-yl]-2-oxa-heptanoic acid.

11. The compound of claim 7 wherein said compound is 7-[7-(3α-Hydroxy-1E-octenyl)-3-oxo-2α, 4α-dioxobicyclo [3.2.1]octan-6-yl]-2-oxa-5Z-heptenoic acid.

12. The compound of claim 7 wherein said compound is 7-[7-(3α-Hydroxy-1E-octenyl)-3-oxo-2α, 4α-dioxobicyclo [3.2.1]octan-6-yl]-2-oxa-5Z-hepten-1-ol.

13. The compound of claim 7 wherein said compound is 7-[7-(3α-Hydroxy-1E-octenyl)-3-oxo-2α, 4α-dioxobicyclo [3.2.1]octan-6-yl]-2-oxa-heptan-1-ol.

14. The method of claim 2 wherein said compound is a compound of formula III,

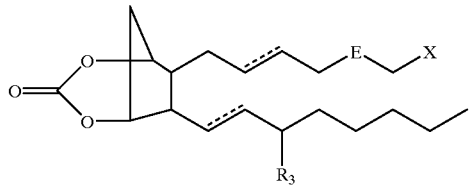

wherein either the α or ω chain may be unsaturated, i.e. the dashed bonds represent a single bond or a double bond which can be in the cis or trans configuration and $R_3$ is =O, —OR, or —O(CO) $R_6$; wherein $R_1$ is hydrogen or an alkyl radical having from 1 to about 5 carbon atoms and $R_6$ is a saturated or unsaturated acyclic hydrocarbon group having from 1 to about 20 carbon atoms, or —$(CH_2)_m R_7$ wherein m is 0–10, and $R_7$ is an aliphatic ring having from about 3 to about 7 carbon atoms, or an aryl radical selected from the group consisting of hydrocarbyl aryl and heteroaryl radicals wherein the heteroatom is selected from the group consisting of nitrogen, oxygen and sulfur atoms; or a pharmaceutically acceptable salt thereof.

15. The method of claim 14 wherein said compound is a compound of formula IV,

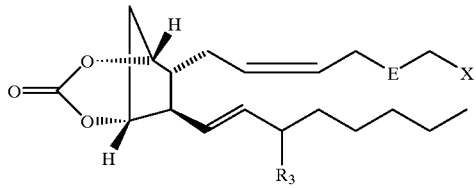

wherein the hatched line indicates the α configuration and the solid triangle indicates the β configuration.

16. The method of claim 14 wherein X is selected from the group consisting of —COOR, —$CH_2OR$, —$CH_2N(R_2)$ and —$C(O)N(R_2)$.

17. The method of claim 15 wherein said compound is selected from the group consisting of
Benzyl 7-[7-(3α-Hydroxy-1E-octenyl)-3-oxo-2α, 4α-dioxobicyclo [3.2.1]octan-6-yl]-2-oxa-heptanoate
Allyl 7-[7-(3α-Hydroxy-1E-octenyl)-3-oxo-2α, 4α-dioxobicyclo [3.2.1]octan-6-yl]-2-oxa-5Z-heptanoate
7-[7-(3α-Hydroxy-1E-octenyl)-3-oxo-2α, 4α-dioxobicyclo [3.2.1]octan-6-yl]-2-oxa-heptanoic acid
7-[7-(3α-Hydroxy-1E-octenyl)-3-oxo-2α, 4α-dioxobicyclo [3.2.1]octan-6-yl]-2-oxa-5Z-heptenoic acid
7-[7-(3α-Hydroxy-1E-octenyl)-3-oxo-2α, 4α-dioxobicyclo [3.2.1]octan-6-yl]-2-oxa-5Z-hepten-1-ol 7-[7-(3α-Hydroxy-1E-octenyl)-3-oxo-2α, 4α-dioxobicyclo [3.2.1]octan-6-yl]-2-oxa-heptan-1-ol.

18. The method of claim 3 wherein said compound is a compound of formula III,

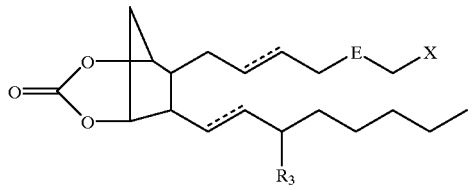

wherein either the α or ω chain may be unsaturated, i.e. the dashed bonds represent a single bond or a double bond which can be in the cis or trans configuration and $R_3$ is =O, —OR, or —O(CO) $R_6$; wherein $R_1$ is hydrogen or an alkyl radical having from 1 to about 5 carbon atoms and $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring having from about 3 to about 7 carbon atoms, or an aryl radical selected from the group consisting of hydrocarbyl aryl and heteroaryl radicals wherein the heteroatom is selected from the group consisting of nitrogen, oxygen and sulfur atoms; or a pharmaceutically acceptable salt thereof.

* * * * *

UNITED STATES PATENT AND TRADEMARK OFFICE
CERTIFICATE OF CORRECTION

PATENT NO. : 6,017,953
DATED : Jan. 25, 2000
INVENTOR(S) : Burk et al

It is certified that error appears in the above-indentified patent and that said Letters Patent is hereby corrected as shown below:

Column 2, line 24; delete "b e" and insert in place thereof --be--
Column 7, line 56; delete "a n" and insert in place thereof --an--
Column 10, line 55; delete "FC" and insert in place thereof --FCC--
Column 11, line 60; delete "w as" and insert in place thereof --was--
Column 12, line 33; delete "i n" and insert in place thereof --in--
Column 12, line 34; delete "115" and insert in place thereof --15--
Column 15, line 14; delete "-OR," and insert in place thereof $--OR_1--$
Column 15, line 17; delete "R7" and insert in place thereof $--R_7--$
Column 15, line 38; delete "-CH2N" and insert in place thereof $-- -CH_2N--$
Column 15, line 39; delete "R2" and insert in place thereof $--R_2--$
Column 15, line 57; delete "460" and insert in place thereof 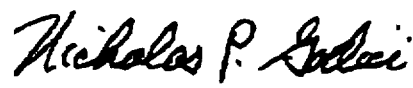
Column 15, line 66; delete "460" and insert in place thereof --4ƶ--
Column 16, line 24; delete "-OR," and insert in place thereof $-- -OR_1--$
Column 18, line 4; delete " -OR," and insert in place thereof $-- -OR_1--$ Signed and Sealed this Thirteenth Day of February, 2001

*Attest:*

NICHOLAS P. GODICI

*Attesting Officer*    *Acting Director of the United States Patent and Trademark Office*